United States Patent [19]
Cox et al.

[11] 4,187,714
[45] Feb. 12, 1980

[54] SURFACE FRICTION TESTER

[75] Inventors: Myron K. Cox, Fairborn; William J. McGrath, Dayton; James E. Cantrill, Fairborn, all of Ohio

[73] Assignee: Wright State University, Dayton, Ohio

[21] Appl. No.: 949,611

[22] Filed: Oct. 10, 1978

Related U.S. Application Data

[63] Continuation of Ser. No. 845,550, Oct. 26, 1977, abandoned.

[51] Int. Cl.$^2$ .................. G01N 19/02; G01P 3/00
[52] U.S. Cl. .................................. 73/9; 73/488
[58] Field of Search .................. 73/9, 8, 7, 488; 280/24, 19, 18; 35/19 R

[56] References Cited

U.S. PATENT DOCUMENTS

| | | | |
|---|---|---|---|
| 715,572 | 12/1902 | Gregg | 280/19 |
| 1,103,619 | 7/1914 | O'Shaughnessy | 280/19 |
| 1,668,593 | 5/1928 | Jones | 73/9 |
| 2,225,140 | 12/1940 | Walker | 73/9 |
| 2,700,297 | 1/1953 | Allen | 73/9 |
| 3,301,039 | 1/1967 | Kummer | 73/9 |
| 3,367,170 | 2/1968 | Lynch | 73/9 |
| 3,431,776 | 3/1969 | Hughes | 73/146 |
| 3,538,742 | 11/1970 | Benning | 73/9 |
| 3,721,115 | 3/1973 | Kearns | 73/9 |
| 3,893,330 | 7/1975 | Shute | 73/9 |

*Primary Examiner*—S. Clement Swisher
*Assistant Examiner*—Denis E. Corr
*Attorney, Agent, or Firm*—Biebel, French & Nauman

[57] ABSTRACT

A surface friction tester in the form of a friction sled which may be pulled over a surface to determine the coefficient of friction of that surface. The sled has a friction surface characterizing a vehicle tire tread attached to the bottom of a base plate. The base plate is a part of a sled frame which also has a tongue portion. A straight spring scale attached to the tongue is used to measure the force required to pull the sled over the surface. The friction sled is especially adapted for accident investigations in order to allow the investigator to determine the coefficient of friction of the surfaces upon which skid marks exist and, thus, calculate the vehicle velocity at the time of brake locking on the basis of the skid marks left by the sliding vehicle.

9 Claims, 4 Drawing Figures

U.S. Patent  Feb. 12, 1980  4,187,714
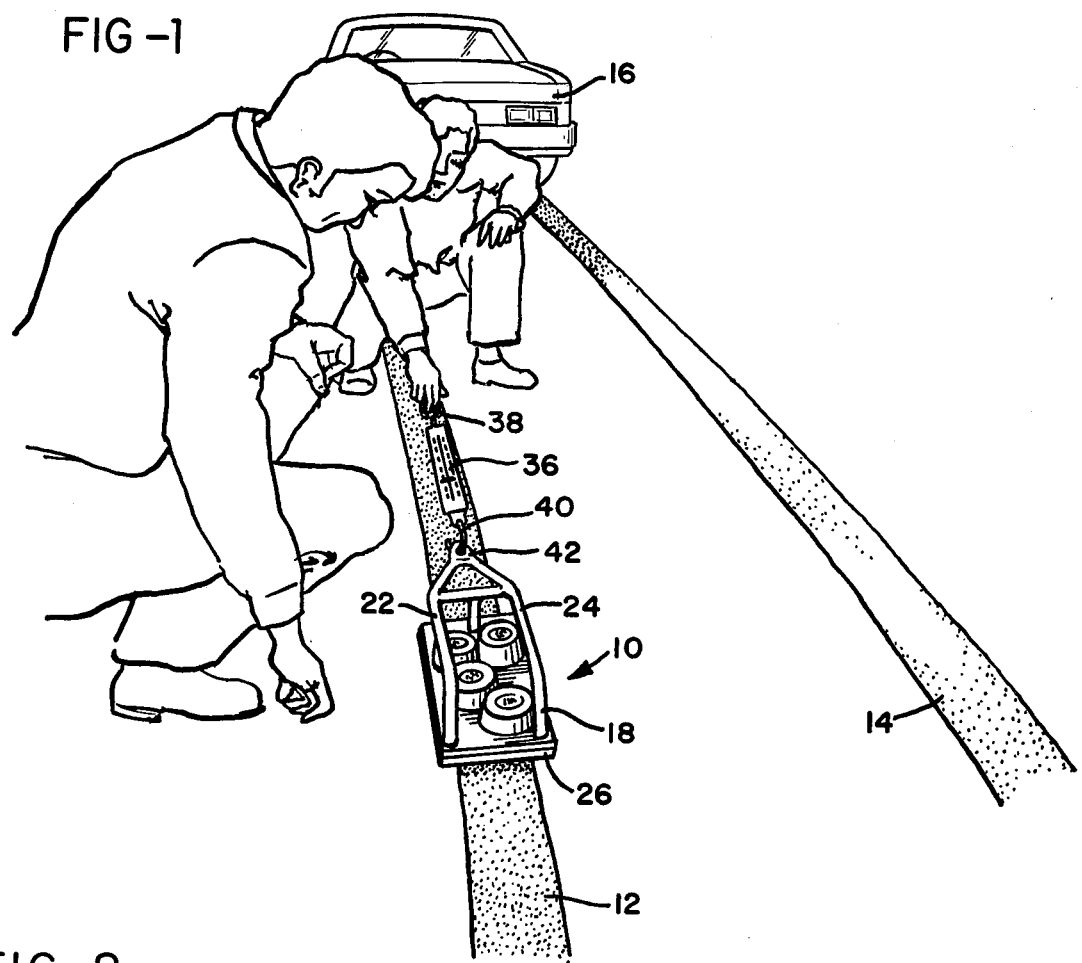
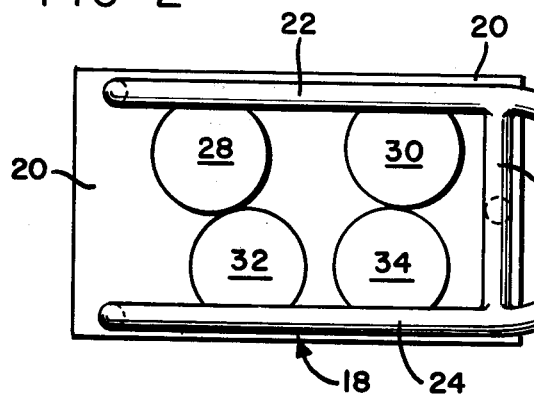
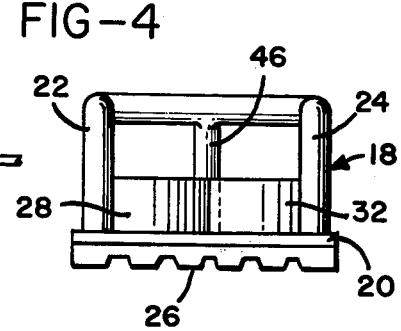
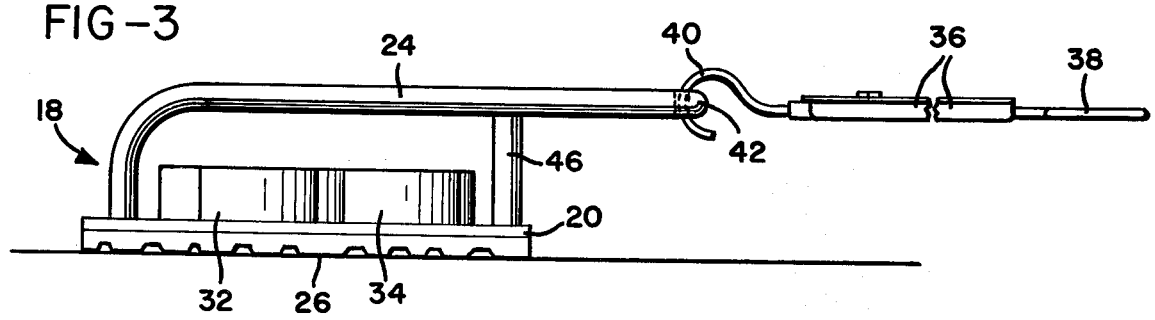

SURFACE FRICTION TESTER

This application is a continuation of U.S. Pat. Ser. No. 845,550; filed October 26, 1977; now abandoned.

BACKGROUND OF THE INVENTION

This invention relates to a surface friction tester and, more particularly, to a portable friction sled which can be used to determine the coefficient of friction of a surface; thereby, enabling accurate calculation of the vehicle velocity at the time of brake locking from the skid marks left by vehicle sliding on that surface.

Traditionally and dutifully the efficient law enforcement officer will measure the length of skid marks which inevitably mark the auto accident scene. Giving attention to procedures for estimating speed based upon the application of the laws of physics (from the point of brake locking) there are a recognized group of scientific procedures to assist the investigator. A very "workable" formula has been used. It is: $V^2 = 30\ f\ s$, where v=velocity (mph) of the auto at the locking of the brakes; f=coefficient of friction of the road surface; and s=feet of measured skid marks.

At present, the investigating officer determines the coefficient of friction (f) by laying down a set of skid marks with his cruiser, applying the brakes at a known velocity. By measuring the skidmarks and utilizing the above given formula, he then calculates the coefficient of friction figure (f) to be used in determining (using the same formula) the speed of the wrecked vehicle at the time of brake lock. However, this equation, through widely used by traffic investigators, is not adequate when the skid conditions occur concurrently and/or consecutively on a variety of road surfaces.

In that instance, it is necessary to use a more complex formula utilizing the various coefficients of friction of the different surfaces over which the vehicle has skid. The problem is that these measurements obviously cannot be obtained by laying down a skid mark with the cruiser since it is difficult and dangerous to try to duplicate such a slide. In addition, there is presently no inexpensive, portable surface friction tester which can be easily used at the accident scene for each of these different surfaces. Rather, the types of surface friction testers known are not totally suitable for that purpose. Instead, they are designed principally for measuring the skid resistance of a highway and not for auto accident investigators, including skid conditions on several different types of surfaces.

As mentioned in Lynch U.S. Pat. No. 3,367,170, there are three general types of apparatus for testing the frictional characteristics of a road surface. First there are devices with a wheel fitted with a brake drum. When the wheel is pulled over a surface, a force is applied to the brake drum, and when this force is great enough to stop the rolling of the wheel, a measure of the frictional characteristic of the road surface is obtained. Most of the ones of this type are automobile or trailer mounted. Patents illustrating this type device are U.S. Pat. Nos. 3,893,330; 3,538,742; 3,431,776 and 2,700,297.

A second type is the British Portable Tester, which is described by Lynch as being a stationary device composed of a stand supporting a pendulum having a rubber shoe on the pendulum. The pendulum is lifted manually and then dropped. The shoe engages the road surface and the loss of energy caused by the shoe sliding on the road surface measured by the distance the pendulum rises to the end of its swing is a measure of the frictional characteristic of the skid resistance of the road surface. The Lynch device is a modification thereof since it utilizes a wheel and pendulum arrangement.

Finally, there is the Penn State Drag Tester. This type of surface friction tester is represented by Kummer U.S. Pat. No. 3,301,039. Kummer states that his device is suitable for use on a slope or a curve or to measure large areas where the laboratory tester (pendulum-type) is unsuitable and the high speed road tester (automobile or trailer mounted wheel-type) cannot be used. The Kummer surface friction tester has a wheeled cart which is pushed in order to drag a shoe over the road surface. A hydraulic chamber, filled with a liquid and communicating with a pressure dial, is used to determine the drag of the shoe, and therefore, to show the skid resistance of the road surface. The hydraulic chamber and its connecting tubing have a volume adjustment according to temperature so that the Kummer surface friction tester can be used under variable conditions of sun, wind and rain.

Still, the hydraulic arrangement is a complicating factor which makes the Kummer device relatively expensive to construct. Besides, as Lynch notes, none of these surface friction testers, including that of Kummer, give entirely satisfactory results under various operating conditions. This is particularly a problem when the coefficient of friction of surfaces (asphalt, concrete, gravel, sand, grass, etc.) must each be measured in order to determine the velocity at the point of brake locking of a wrecked vehicle from the skid marks remaining.

Accordingly, the need exists for an inexpensive, portable surface friction tester which can be used under such conditions to determine the coefficient of friction of various surfaces in making an accident report.

SUMMARY OF THE INVENTION

The present invention meets that need by providing a portable friction sled which can be pulled over various types of surfaces in following along the skid marks of a sliding vehicle. In this manner the different coefficients of friction of the various surfaces traversed by the skid marks can be easily determined. This, in turn, enables the accident investigator to calculate the vehicle velocity at the time of brake lock.

The friction sled of the instant invention has a frame with a relatively flat base plate, to the bottom of which there is attached a friction surface. The friction surface should have a composition, tread depth, etc., similar to the tire tread of the vehicle which left the skid marks under investigation, although, other friction surfaces can be used. Generally, it may be an appropriately sized piece of rubber tire tread which is adhered to the base plate of the sled frame.

The base plate of the sled frame may also be used to support weight means on its upper surface for providing a suitable load factor. Preferred for the weight means are solid lead weights which may be uniformly spaced on the base plate to give the loading desired. The lead weights may be either permanently attached, temporarily attached, or merely seated onto the base plate. Other types of weight means and other attachment locations on the sled frame may be used.

The frame also has a tongue portion to which a straight spring scale is attached. A pull means at the end of the scale opposite the tongue attachment is used to pull the friction sled over the surface to be tested. While it is not necessary that the skid marks be followed in making the coefficient of friction measurement, with the preferably sized friction sled this is possible.

At any rate, by pulling at one end of the spring scale, with the sled frame attached to the other end, measurement is obtained which will give the coefficient of friction. Thus, the spring scale measures the force applied in order to pull the friction sled at a smooth, steady rate over the surface. That figure may be a weight unit (pounds or grams). Using the ratio of scale indicated amount to weight of the friction sled (in the same units), this yields the unitless coefficient of friction figure (f). Alternatively, for a weight sled, the scale can be calibrated for a direct coefficient of friction indication (f). It is this (f) figure which can be used in the formulas along with the measured length of the skid mark to calculate the velocity of the vehicle at the time of brake lock.

As mentioned for skid marks on a single type of surface, the formula used is $V^2 = 30$ fS, where v=velocity (mph), f=coefficient of friction, S=feet of measured skid marks. The factor 30 is in mph/ft., and represents 2g/2.15, where g is 32.2 ft./sec$^2$ and 2.15 is a correction factor which expresses units of velocity in miles per hour and distances of skid marks in feet, i.e., $(5280/3600)^2 = 2.15$. This equation is based on the assumption that all the vehicle's weight is carried on the braking wheels, i.e., all of the vehicle's tires must be skidding; the automobile slides to a complete stop; and that the slide is on a level surface.

If there are two wheels on one surface and two wheels on another, then the formula used is $V^2 = 15$ S $(f_1 + f_2)$. Where $f_1$ is the coefficient of friction of the surface on which the one set of wheels slide and $f_2$ is the coefficient of friction of the surface on which the second set of wheels slide. When the situation is one where the vehicle has started to skid on one type of road surface and terminated on an entirely different type of surface, the formula used is $V^2 = 30$ $(f_1S_1 + f_2S_2)$, where $f_1$ and $S_1$ are the coefficient of friction and skid distance on the first surface and $f_2$ and $S_2$ are the figures for the second surface traversed by the skid marks.

Generally using these three formulas, or combinations thereof, and in conjunction with the surface friction tester of the present invention, it is possible under most conditions to calculate the velocity of the vehicle at the time of brake lock. This is true provided the brakes remained locked throughout the stopping distance and provided the vehicle did not hit some object such as another car, abutment, tree, etc., that would absorb part of the kinetic energy. If it did hit something that assisted in the stop, then only the minimum speed at the start of the skid can be determined. But this alone may be determinative of liability in a collision where the minimum speed of one car, for example, exceeded the limit.

As will be apparent, the friction sled of the present invention while especially adapted for accident investigations, may be used in any number of other situations to determine the coefficient of friction of a surface. Its advantages are also apparent. It is simple and inexpensive. It is easily handled and transported. The load may be varied simply by adding to or subtracting from the weight means. It can be used on any type of surface, without the need to obtain high speeds, use a pendulum, or be borne by a wheeled cart. And yet, despite its simplicity and inexpensiveness, it has proven to have an error factor of only ±1% of the usual method of calculation using the cruiser to lay down a duplicate set of skid marks.

Accordingly, it is an object of the present invention to provide a portable friction surface tester which can be used to determine the coefficient of friction of road surfaces in investigating an automobile accident.

Other objects and advantages of the invention will be apparent from the following description, the accompanying drawing and the appended claims.

BRIEF DESCRIPTION OF THE DRAWING

FIG. 1 is a perspective view of the friction sled of the present invention in use;

FIG. 2 is a partial top plan view of the friction sled of the present invention;

FIG. 3 is a side plan view thereof; and

FIG. 4 is a rear plan view thereof.

DESCRIPTION OF THE PREFERRED EMBODIMENTS

Referring to FIG. 1, there is shown the surface friction tester 10 of the present invention being used to determine the coefficient of friction of the road surface upon which skid marks 12 and 14 are evident. This illustrates how the device would be used as an aid in calculating the velocity of vehicle 16 at the time of brake locking on the basis of the skid marks left by the sliding vehicle.

FIGS. 2–4 show in more detail the friction sled itself, in its preferred embodiment. Thus, the friction sled body comprises a frame 18 having a rectangular base plate 20 and side bars 22 and 24 attached thereto. These parts may be formed of a metal such a steel. Base plate 20 is relatively flat, and may be a 7"×12" sheet of one-eight inch steel. It has a friction surface 26 adhered to its bottom surface. This may be done by use of an epoxy adhesive, for example.

Friction surface 26 as shown characterizes an automobile tire tread. In fact, it may be a piece of tire tread which is cut to size and adhered to base plate 20. Alternatively, it may be a formed rubber surface which duplicates the characteristics of the tread of the vehicle which it is desired to determine the coefficient of friction with respect to the surface tested. It may even be a steel plate characterizing the vehicle body in order to enable determination when the car flips on its side for a part of the sliding distance.

The upper surface of base plate 20 is used in the preferred embodiment as the support for lead weights 28, 30, 32 and 34. The lead weights shown are solid, three-inch diameter discs, weighing five pounds each. Various other weight means and loading arrangements can be used, but the one shown involves four lead weights 28, 30, 32 and 34 of five pounds each spaced on base plate 20. These weights are removable. They may be adjusted in number and weight to change the loading or in arrangement to balance the load on the frame 18. Likewise, weights may be permanently affixed to the base plate 20, hung from side bars 22 and 24, or arranged in other ways to provide appropriate weight means.

In the illustrated embodiment, the twenty pounds provided by the weight means and the eight and one-fourth pounds provided by the rest of the friction sled body gives it a total weight of 28¼ pounds. This amount may be used as the denominator in the equation f=x/w where f is the coefficient of friction, w is the weight of the friction sled body, and x is the figure shown on the scale as the friction sled is pulled in a smooth, steady state over the surface being tested.

As shown in FIGS. 1 and 3, the scale 36 may be a straight spring scale, such as a Chatillon Straight Spring Scale, which measures pounds in at least as small as quarter pound units. An appropriate circular spring scale could also be used. A thirty, forty or fifty pound scale may be used with the 28¼ pounds sled body. The friction sled is pulled over the surface to give a steady reading on the scale, say 19¾ pounds. Using the ratio of scale figures to weight of dead body, this means that a coefficient of friction of 0.7 is indicated. Obviously, a scale which is calibrated to read in figures representing a coefficient of friction could be used as long as a set weight friction sled body is used.

The pulling of the friction sled is done manually by pull means 38 which is located at one end of the scale 36. The other end of the scale 36 is attached by hook 40 to the tongue 42 of the friction sled body. Other scale attachment means may be used as long as it is possible to exert a uniform pulling force through pull means 38 and scale 36 to the sled body.

In the shown embodiment side bars 22 and 24 converge approximately seven inches beyond the front edge of base plate 20 to form tongue 42. Cross-bar 44 and center post 46 are used to distribute the pulling force uniformly to the friction sled body from tongue 42. The upper portion of the frame consisting of side bars 22 and 24, cross-bar 44 and tongue 42 is elevated above base plate 20 approximately three inches in this preferred embodiment.

As can be seen, the preferred embodiment is a compact, relatively lightweight (28¼ lbs.) device which can be easily transported and used in making the measurements of the coefficient of friction of the surface. It is a handy tool for the accident investigator making calculations based on skid marks, and can clearly be used in many other situations to determine surface friction.

While the product herein described constitutes a preferred embodiment of the invention, it is to be understood that the invention is not limited to this precise product, and that changes may be made therein without departing from the scope of the invention.

What is claimed is:

1. A portable surface friction tester in the form of a friction sled comprising:
    (a) a frame having a relatively flat rectangular base plate with front and rear edges of a lesser dimension than the lateral edges thereof and having side bars elevated above said base plate, said side bars extending substantially the length of said base plate along each lateral edge and joined to said base plate at each corner of the rear edge and the lateral edge, said bars also converging beyond said front edge to form a tongue;
    (b) a friction surface attached to the bottom of said base plate and characterizing a vehicle tire tread,
    (c) weight means supported by said frame for loading said friction sled,
    (d) pull means connected to said tongue by which said friction sled can be pulled over the surface to be tested, and
    (e) a scale intermediate said pull means and said tongue to provide a measurement giving the coefficient of friction of the surface to be tested as said friction sled is pulled in a smooth, steady state over that surface.

2. A portable friction tester as in claim 1 wherein said friction surface is an automobile tire tread adhered to the bottom of said base plate.

3. A portable friction tester as in claim 2 wherein said base plate is 7×12 inches, and said friction sled weighs, including said weight means, twenty-eight and one-quarter pounds.

4. A method for determining at least the minimum speed of a skidding vehicle at the time of accident by determining the coefficient of friction of the various road surfaces over which the vehicle skidded and measuring the length of skid marks left by the vehicle at the accident scene, comprising the steps of:
    (a) measuring the length of the skid marks left by the vehicle from the time of brake locking,
    (b) pulling a portable friction sled at a smooth, steady rate over the surface or surfaces over which the skid marks exist and for which the coefficient of friction is to be measured,
    said friction sled having a frame with a relatively flat base plate and a frame structure connected to said base plate and having a friction surface attached to the bottom of said base plate and characterizing a vehicle tire tread,
    said friction sled further having pull means connected to an elevated attachment means and a scale intermediate said pull means and attachment means,
    (c) utilizing the reading on said scale means as said friction sled is pulled over the surface or surfaces to determine the coefficient of friction of said surface or surfaces, and
    (d) determining at least the minimum speed of said vehicle at the time of accident on the basis of the determined coefficient of friction of said surface or surfaces and the measured length of said skid marks.

5. The method of claim 5 wherein said scale is a spring scale which gives readings in weight units, and said coefficient of friction is a ratio of the reading on said scale and the weight of said friction sled.

6. The method of claim 4 wherein said scale is a spring scale which has been calibrated to give a direct coefficient of friction indication.

7. The method of claim 4 wherein said skid marks are evident on several different types of surfaces and said friction sled is pulled over each to give the coefficient of friction of each.

8. The method of claim 4 wherein friction surface is an automobile tire tread adhered to the bottom of said base plate.

9. The method of claim 4 wherein said friction sled further includes removable weight means which may be used to adjust the loading on said friction sled.

* * * * *

UNITED STATES PATENT AND TRADEMARK OFFICE
CERTIFICATE OF CORRECTION

PATENT NO. : 4,187,714
DATED : February 12, 1980
INVENTOR(S) : Myron Cox, William McGrath, James E. Cantrill It is certified that error appears in the above-identified patent and that said Letters Patent are hereby corrected as shown below:

Column 6, line 43 (Claim 5), "5" should be --4--.

Signed and Sealed this

Tenth Day of June 1980

[SEAL]

Attest:

SIDNEY A. DIAMOND

Attesting Officer

Commissioner of Patents and Trademarks